(12) United States Patent
Schoonbaert

(10) Patent No.: US 10,709,311 B2
(45) Date of Patent: Jul. 14, 2020

(54) VIDEO LARYNGOSCOPE WITH MONITOR STABILIZATION

(71) Applicant: Ian Schoonbaert, Calgary (CA)

(72) Inventor: Ian Schoonbaert, Calgary (CA)

(73) Assignee: Montane Medical Corporation, Calgary (CA)

( * ) Notice: Subject to any disclaimer, the term of this patent is extended or adjusted under 35 U.S.C. 154(b) by 68 days.

(21) Appl. No.: 15/975,983

(22) Filed: May 10, 2018

(65) Prior Publication Data

US 2019/0082932 A1 Mar. 21, 2019

Related U.S. Application Data

(60) Provisional application No. 62/504,755, filed on May 11, 2017.

(51) Int. Cl.
| | |
|---|---|
| *A61B 1/267* | (2006.01) |
| *A61B 1/00* | (2006.01) |
| *A61B 1/045* | (2006.01) |

(52) U.S. Cl.
CPC ...... *A61B 1/00048* (2013.01); *A61B 1/00016* (2013.01); *A61B 1/00039* (2013.01); *A61B 1/00052* (2013.01); *A61B 1/045* (2013.01); *A61B 1/267* (2013.01)

(58) Field of Classification Search
CPC .... A61B 1/00039–00055; A61B 1/045; A61B 1/267–2676
See application file for complete search history.

(56) References Cited

U.S. PATENT DOCUMENTS

| | | | | |
|---|---|---|---|---|
| 8,641,605 | B2* | 2/2014 | Shoroji | A61B 1/00052 600/178 |
| 8,715,172 | B1* | 5/2014 | Girgis | A61B 1/05 600/188 |
| 9,095,298 | B2* | 8/2015 | Ashcraft | A61B 1/267 |
| 9,468,367 | B2* | 10/2016 | Ouyang | A61B 1/00103 |
| 9,498,112 | B1* | 11/2016 | Stewart | A61B 1/267 |
| 2002/0022769 | A1* | 2/2002 | Smith | A61B 1/00052 600/188 |
| 2003/0195390 | A1* | 10/2003 | Graumann | A61B 1/00016 600/188 |
| 2011/0270038 | A1* | 11/2011 | Jiang | A61B 1/00052 600/188 |
| 2013/0018227 | A1* | 1/2013 | Schoonbaert | A61B 1/00052 600/188 |

(Continued)

*Primary Examiner* — Nicholas J Plionis
*Assistant Examiner* — Steven J Cotroneo
(74) *Attorney, Agent, or Firm* — Ryan W. Dupuis; Ade & Company Inc.; Kyle R. Satterthwaite

(57) ABSTRACT

A laryngoscope device with an elongate handle includes a video laryngoscope blade with a camera mounted transversely on a first end of the handle and one or more pivot assemblies coupling a display monitor on an opposing second end of the handle. Each pivot assembly includes a pivot coupling defining a respective axis of rotation of the display monitor relative to the handle and a motor for controlling angular position of the display monitor relative to the handle about the respective axis. A sensor device is arranged to detect movement of the display monitor away from a target orientation such that a controller having the target orientation stored thereon can be adapted to operate the motor to return the display monitor to the target orientation.

18 Claims, 8 Drawing Sheets

(56) References Cited

U.S. PATENT DOCUMENTS

| | | | | |
|---|---|---|---|---|
| 2014/0148808 A1* | 5/2014 | Inkpen | ............... | G01B 7/003 |
| | | | | 606/80 |
| 2015/0002490 A1* | 1/2015 | Han | ............... | A61B 8/462 |
| | | | | 345/204 |
| 2016/0302653 A1* | 10/2016 | Inoue | ............... | G06T 7/593 |
| 2018/0191959 A1* | 7/2018 | Neufeldt | ............... | G03B 17/561 |
| 2018/0206705 A1* | 7/2018 | Chan | ............... | A61B 1/00048 |
| 2018/0308241 A1* | 10/2018 | Johnston | ............... | G06T 7/248 |
| 2019/0150714 A1* | 5/2019 | Onishi | ............... | A61B 1/00147 |

\* cited by examiner

VIDEO LARYNGOSCOPE WITH MONITOR STABILIZATION

This application claims the benefit under 35 U.S.C.119(e) of U.S. provisional application Ser. No. 62/504,755, filed May 11, 2017.

FIELD OF THE INVENTION

The present invention relates to a video laryngoscope device of the type which capturing and displaying a video image of the glottis of a patient to assist an operator in placing an endotracheal tube into the patient, and more particularly the present invention relates to a video laryngoscope device in which a display monitor for displaying the video images of the glottis to the operator is supported on a handle of the laryngoscope using at least one controlled pivot assembly which supports the display monitor in a target orientation regardless of the orientation of the handle.

BACKGROUND

A video laryngoscope is a relatively new development in the field of anaesthesia.

Traditional DIRECT LARYNGOSCOPY (DL) involves using a blade with a light at the end to obtain a view of the glottis via a direct view from the maxillary teeth to the vocal cords. This allows passage of an endotracheal (ET) tube under direct vision. Direct laryngoscopy involves alignment of the oral, pharyngeal and tracheal axes to produce this view.

RIGID INDIRECT LARYNGOSCOPY (RIL) involves obtaining a view of the glottis without alignment of the oral, pharyngeal and tracheal axes. This view is obtained with prisms, mirrors and fibre-optics in the past and more recently with video cameras (i.e. CMOS or CCD camera).

Although initially used primarily as rescue devices (i.e. when DL has failed) video laryngoscopes are being increasingly used as primary devices as well. Given that the view of the glottis is obtained by a video camera, the image obtained has to be displayed on a monitor for the user to guide the placement of an ET tube. There are two primary monitor types as described in the following.

The first type of monitor is external and does not move relative to the position/angle of the handle and is in a fixed position relative to the user. The advantage is that the monitor is always in the same position relative to the user. The disadvantages are that adjusting the monitor would require abandoning the attempt or a second person available to adjust the monitor and that the monitor is often out of the immediate field of view of the user. The user must look at the mouth of the patient during the attempt to place the VL blade, to advance the VL blade, to suction the airway and to place the ET tube into the mouth. Therefore, having the monitor out of the immediate line of site of the user may cause them to lose situational awareness of the patient during the attempt while the user glances between the monitor and the patient.

To address the deficiencies of the first type of monitor, the second monitor type is a monitor mounted on the handle, typically on a "hinge" that allows the user to vary the angle of the monitor relative to the handle to the user's preference in one to three axes (pitch, roll and/or yaw). Once in position, the monitor will stay in a fixed position relative to the handle until manually re-positioned by the user. The advantage is that the monitor and the patient's mouth is always in the immediate field of view of the user. The disadvantage is that the once the procedure is started adjusting the monitor's position relative to the handle would require using the users right hand (which then can't be used for suction or holding the ET tube) or adjusting the user's head to allow a better view of the monitor. As intubation is a dynamic process that requires the handle to move through a range of angles during the intubation attempt this means that at certain times during the attempt, the monitor will be at a less than ideal angle relative to the user (see FIG. 1).

SUMMARY OF THE INVENTION

According to one aspect of the invention there is provided a laryngoscope device comprising:

a handle which is elongate in a longitudinal direction between opposing first and second ends;

a laryngoscope blade supported on the first end of the handle so as to extend outwardly from the handle transversely to the longitudinal direction of the handle;

a camera supported on laryngoscope blade so as to be arranged to capture video images;

a display monitor for displaying the video images captured by the camera;

at least one pivot assembly comprising:
  a pivot coupling the display monitor to the second end of the handle for pivotal movement about a respective axis of the pivot; and
  a motor for controlling angular position of the display monitor relative to the handle about the axis of the pivot;

a sensor device arranged to detect movement of the display monitor away from a target orientation; and a controller having the target orientation stored thereon and being adapted to operate the motor of said at least one pivot assembly responsive to detection by the sensor device that the display monitor has been displaced away from the target orientation.

This invention uses a gimbal design to link the handle of any type of video laryngoscope to the monitor mounted directly on the handle. A gimbal is a device that permits a body to incline freely in any direction or suspends it so that it will remain level when it's support is tipped. In this way, the monitor module can be kept in a stable position relative to the horizon regardless of the position of the handle. Using a 3-axis gimbal set, with the outermost gimbal attached to the handle, and each successive gimbal mounted on the other with orthogonal pivot axes and the monitor mounted on the innermost gimbal will allow the monitor to remain independent of the rotation of it's support—the handle (see FIG. 2, 3).

Preferably the target orientation stored on the controller is controllably adjustable by an operator, for example through an operator input supported externally on the laryngoscope device. The operator input may be supported on the handle and may comprise a joystick for example. Preferably the operator input is located so as to be adapted to be readily accessible by a thumb of a hand of an operator gripping the handle of the laryngoscope device therein.

The target orientation stored on the controller may alternatively be adjustable through a wireless connection with an external mobile computer device.

The sensor device may include an inertial measurement unit supported in fixed relation to the display monitor so as to be arranged to measure accelerations acting on the display monitor. The sensor device in this instance may further comprise a second inertial measurement unit supported in fixed relation to the handle so as to be arranged to measure accelerations acting on the display monitor.

The sensor device may further comprise an angular position sensor supported on the pivot of said at least one pivot assembly to measure angular position of the display monitor relative to the handle about the axis of the pivot of said at least one pivot assembly, in which the controller uses the measured angular position in controlling the motor of said at least one pivot assembly.

The pivot assembly may include (i) one pivot in which the pivot axis thereof is a pitch axis oriented parallel to a display surface of the display monitor and transversely to the handle, (ii) one pivot in which the pivot axis thereof is a roll axis oriented perpendicularly to a display surface of the display monitor and transversely to the handle, and/or (iii) one pivot in which the pivot axis thereof is a yaw axis oriented parallel to the longitudinal direction of the handle, or any combination thereof. Accordingly, in one embodiment the pivot assembly includes two pivots in which the pivot axes thereof are oriented perpendicularly to one another, and in another embodiment the pivot assembly includes three pivots in which the pivot axes thereof are oriented transversely to one another.

Optionally, a tracking camera may be supported on the display monitor so as to be arranged to capture an image of the operator such that tracking programming stored on the controller can be executed by the controller to identify the operator in the images captured by the tracking camera and to operate the motor of said at least one pivot assembly so as to maintain the operator centred within the images captured by the tracking camera.

Preferably a battery is supported on the handle which is operatively connected to supply electrical power to each one of the camera, the display monitor, the sensor device, the controller, and the motor of said at least one pivot assembly.

BRIEF DESCRIPTION OF THE DRAWINGS

Various embodiments of the invention will now be described in conjunction with the accompanying drawings in which.

In the drawings like characters of reference indicate corresponding parts in the different figures.

DETAILED DESCRIPTION

Figure 1:
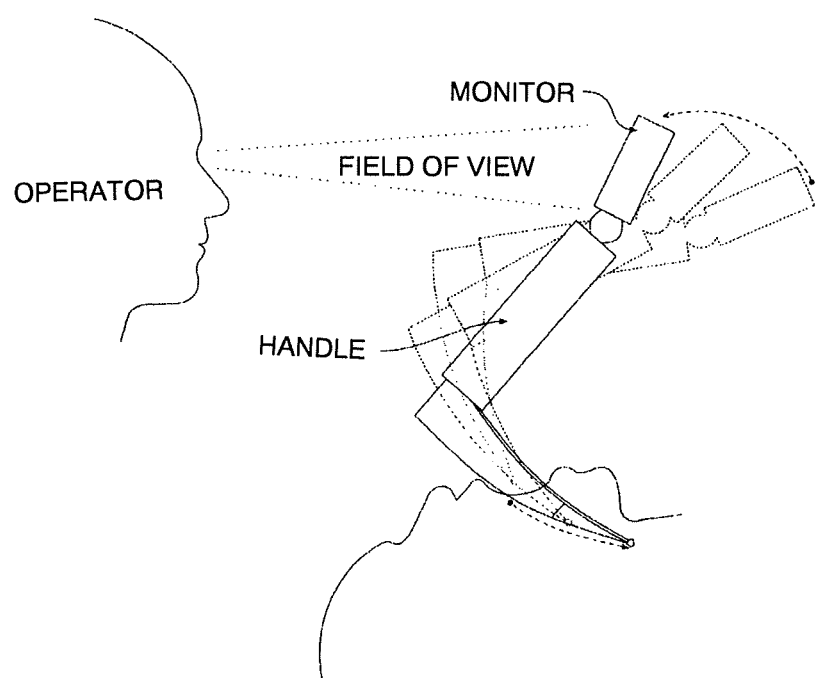
FIG. 1 is a partly sectional side elevational view of an operator inserting a conventional laryngoscope into a patient.
Figure 2:
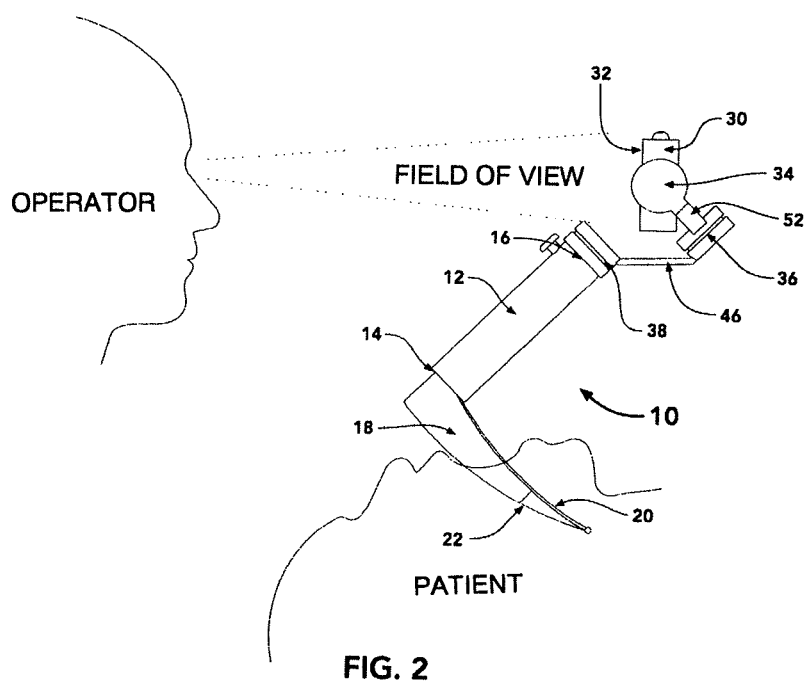
FIG. 2 is a partly sectional side elevational view of an operator inserting the laryngoscope device according to a first embodiment of the present invention into a patient.

Referring to the accompanying figures there is illustrated a laryngoscope device generally indicated by reference numeral 10. The device 10 is particularly suited for use in laryngoscopy procedures. Laryngoscopy is endoscopy of the larynx, a part of the throat. It is a medical procedure that is used to obtain a view of the vocal folds and the glottis, for example, to facilitate tracheal intubation during anaesthesia or cardiopulmonary resuscitation or for surgical procedures on the larynx or other parts of the upper tracheobronchial tree.

Although various embodiments of the device are described and illustrated herein, the features in common with the various embodiments will first be described. The device 10 includes an elongate handle 12 which is elongate in a longitudinal direction between a first end 14 and an opposing second end 16. The handle is generally cylindrical in shape and sized so as to be suitably gripped within a single hand of an operator.

A laryngoscopy blade 18 is mounted on the first end 14 of the handle to extend outward in a generally radial direction relative to the longitudinal direction of the handle. In the illustrated embodiment, the blade is shown to be a Mac style blade in which the blade is curved so as to be concave along an inner side 20 thereof which faces longitudinally towards the opposing second end of the handle, while being convex along an outer side 22 which faces longitudinally outward away from the second end of the handle. In further embodiments however, the laryngoscopy blade 18 may take any other form or shape without affecting the function of the stabilization of the display monitor as described herein.

A camera 24 is provided on the device 10 for capturing video images. The camera may be mounted towards the outermost tip of the blade so as to be suitably arranged for capturing images of the glottis of the patient as the blade is inserted into the patient.

A light 26 is also provided in association with the camera to provide suitable illumination for capturing images with the camera. The light 26 may take the form of an LED light mounted on the blade, however, any other suitable form of illumination for the camera may be used.

A battery 27 may be mounted in the handle to supply electrical power for the camera and the light as required.

A controller 28 is also supported on the device 10, typically within the handle 12, to provide control of the camera and the light source as directed by the operator. The controller includes a processor and a memory storing programming thereon which is arranged to be executed by the processor for performing the various functions described herein.

A display monitor 30 is supported on the device 10 in operative connection to the controller to receive power from the battery and for displaying images captured by the camera 24 on a display surface 32 of the monitor.

A gimbal assembly of various configurations described herein is used for coupling the display monitor relative to the second end of the handle 12 such that the display monitor can be pivoted relative to the handle about one or more pivot axes of respective pivoted assemblies 34, 36, and 38 as described in further detail below.

Turning now to the first embodiment of FIGS. 1 through 10, the device 10 in this instance comprises a gimbal assembly formed of three pivot assemblies, in which each pivot assembly assists in coupling the display monitor relative to the handle for pivotal movement about a respective pivot axis thereof, and in which the three pivot axes are oriented substantially perpendicularly to one another in a neutral position of the display monitor relative to the handle.

More particularly the gimbal assembly includes a first pivot assembly including a first pivot 34 that is directly coupled to the display assembly to support the display monitor for pivotal movement about a first pitch axis of the first pivot assembly. The first pitch axis is typically horizontally oriented in use so as to be perpendicular to the longitudinal direction of the handle and perpendicular to the blade 18 in a neutral position of the device. The first pitch axis is thus parallel to the display surface 32 of the display monitor. A pitch motor 35 is coupled to the first pivot 34 and controls the angular position of the pivot which in turn controls the angular position of the display monitor relative to the handle about the first pitch axis of the gimbal assembly.

The gimbal assembly also includes a second pivot assembly including a second pivot 36 coupled between the first pivot 34 and a third pivot 38 of a third pivot assembly. The second pivot 36 supports the display monitor for pivotal movement about a second roll axis of the second pivot assembly. The second roll axis is typically horizontally oriented in use so as to be perpendicular to the longitudinal direction of the handle while being parallel to the blade 18 in a neutral position of the device. The second roll axis is thus generally perpendicular to the display surface 32 of the display monitor in the neutral position. A roll motor 37 is coupled to the second pivot 36 and controls the angular position of the pivot which in turn controls the angular position of the display monitor relative to the handle about the second roll axis of the gimbal assembly.

The third pivot 38 is directly coupled to the second end of the handle to support the display monitor for pivotal movement about a third yaw axis of the third pivot assembly. The third yaw axis is typically oriented in the longitudinal direction of the handle so as to be generally perpendicular to the first pitch axis and the second roll axis in the neutral position of the device 10. The third yaw axis is generally parallel to the display surface 32 of the display monitor in the neutral position. A yaw motor 39 is coupled to the third pivot 38 and controls the angular position of the pivot which in turn controlled the angular position of the display monitor relative to the handle about the third yaw axis of the gimbal assembly.

In the illustrated embodiment, the third pivot 38 includes a first portion 42 fixed relative to the handle and a second portion 44 which rotates relative to the first portion about the yaw axis. An intermediate frame member 46 is in turn coupled between the second portion 44 of the third pivot and a corresponding portion of the second pivot 36.

The second pivot 36 includes a first portion 48 fixed to the frame member 46 and a second portion 50 which rotates relative to the first portion about the roll axis. Another intermediate frame member 52 is in turn coupled between the second portion 50 of the second pivot and a corresponding portion of the first pivot 34.

The first pivot 34 includes a first portion 54 fixed to the frame member 52 and a second portion 56 which rotates relative to the first portion 54 about the pitch axis. The second portion 56 mounts the display monitor in fixed relation thereon.

The device 10 further includes a sensor assembly of various forms which is used to detect movement of the display monitor away from a target orientation stored on the memory of the controller. In the first embodiment illustrated in FIGS. 1 through 10, the sensor assembly includes a first inertial measurement unit 58 supported in fixed relation to the display monitor. The inertial measurement unit is an electronic device that measures and reports the specific force or acceleration that the body of the display monitor undergoes, in addition to an angular rate, using a combination of accelerometers and gyroscopes. The inertial measurement unit 58 thus senses the amount and rate of change of any movement of the display monitor away from an initial target orientation about all three axes of the gimbal assembly.

In some embodiments, the sensor assembly may further include a second inertial measurement unit 60 supported in fixed relation to the handle. The second inertial measurement unit is identical in configuration to the first inertial measurement unit so as to sense the amount and rate of change of any movement of the handle away from a previous position of the handle about all three axes of the gimbal assembly.

The sensor device may yet further include an angular position sensor 62 associated with each of the pivots 34, 36 and 38 so as to measure the angular position of the first portion of the pivot relative to the second portion of the pivot in each instance. The measured angular positions of the sensors 72 are reported back to the controller in real time similarly to the measured data from both the first and second inertial measurement units.

Typically, the inertial measurement unit 58 on the display monitor is sufficient by itself to provide feedback to the controller for operating the motors to maintain the display monitor in the target orientation, however, the addition of a second inertial measurement unit can provide more precise control of the position of the display monitor. Alternatively, only the second inertial measurement unit on the handle together with the angular position sensors 62 may be used as input to the controller to detect movement of the handle relative to the surroundings and detect movement of the display monitor relative to the handle which allows determination of any movement of the display monitor relative to the surroundings.

Figure 3:
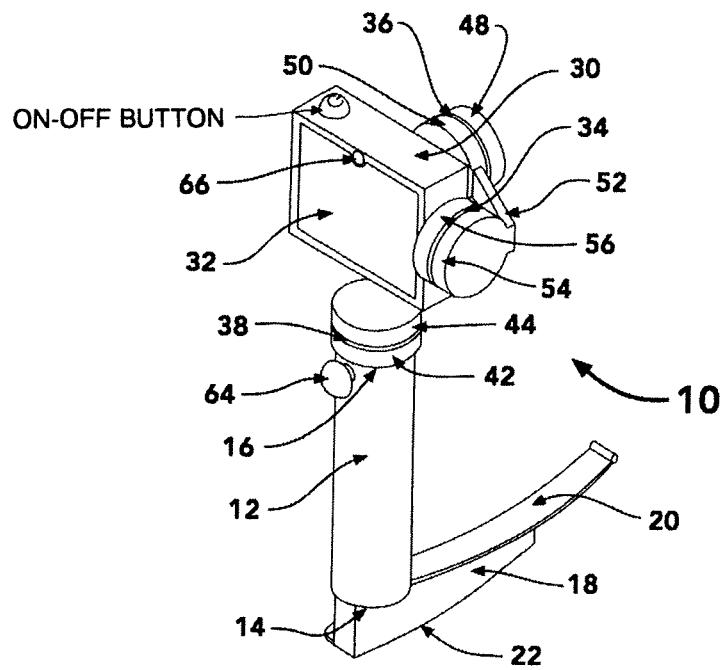
FIG. 3 is an isometric view of the laryngoscope device according to the first embodiment of FIG. 1.
Figure 4:
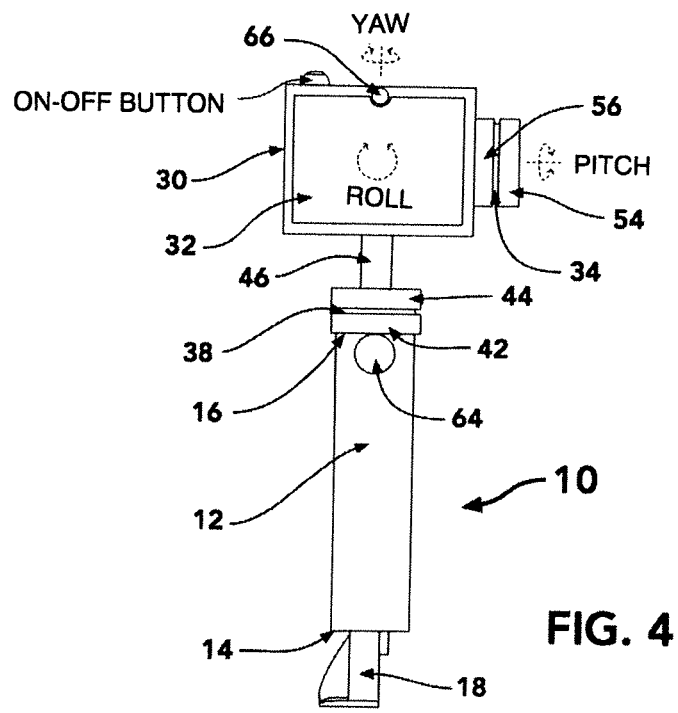
FIG. 4 is a front elevational view of the laryngoscope device according to the first embodiment of FIG. 1.
Figure 5:
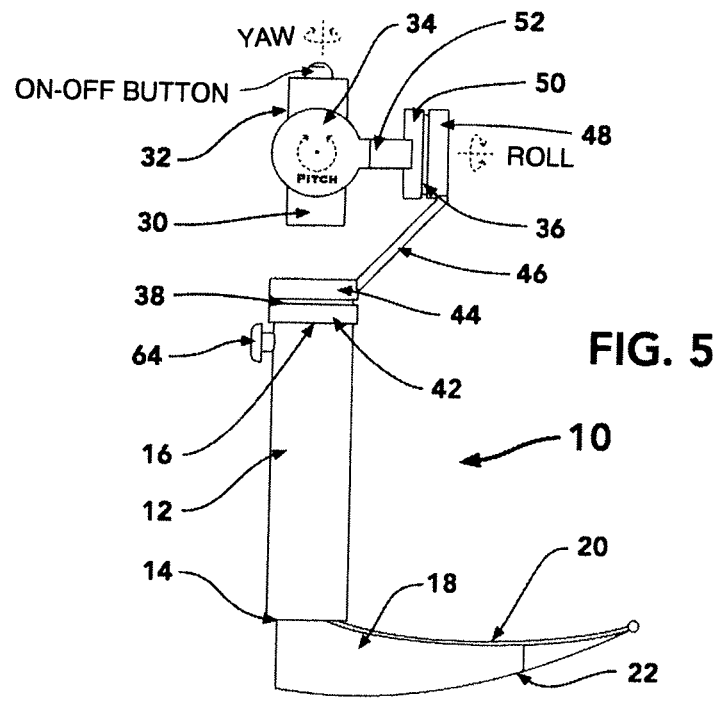
FIG. 5 is a side elevational view of the laryngoscope device according to the first embodiment of FIG. 1.
Figure 6:
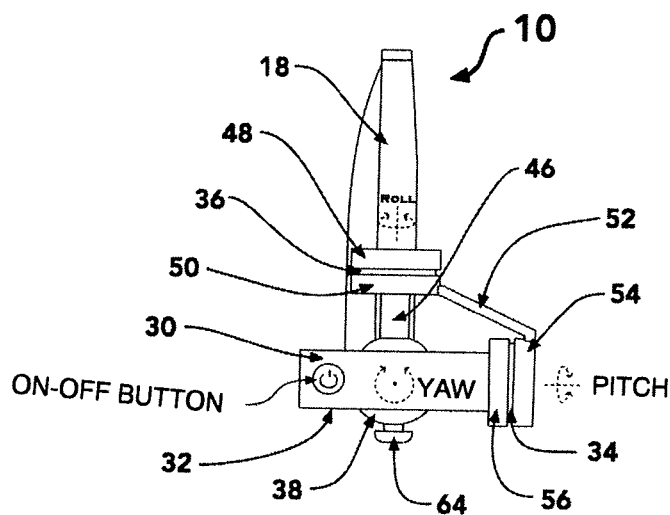
FIG. 6 is a top plan view of the laryngoscope device according to the first embodiment of FIG. 1.
Figure 7:
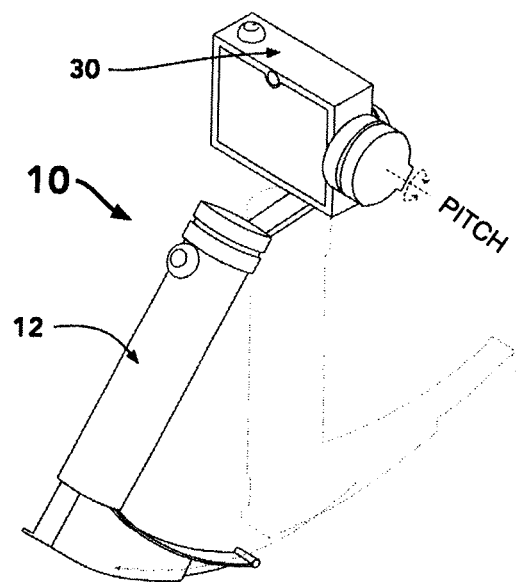
FIG. 7 is an isometric view of the laryngoscope device according to the first embodiment of FIG. 1 as the display monitor pivots about a pitch axis relative to the handle.
Figure 8:
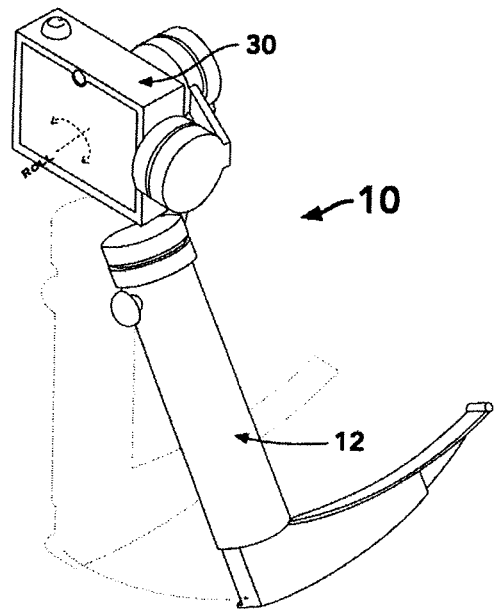
FIG. 8 is an isometric view of the laryngoscope device according to the first embodiment of FIG. 1 as the display monitor pivots about a roll axis relative to the handle.
Figure 9:
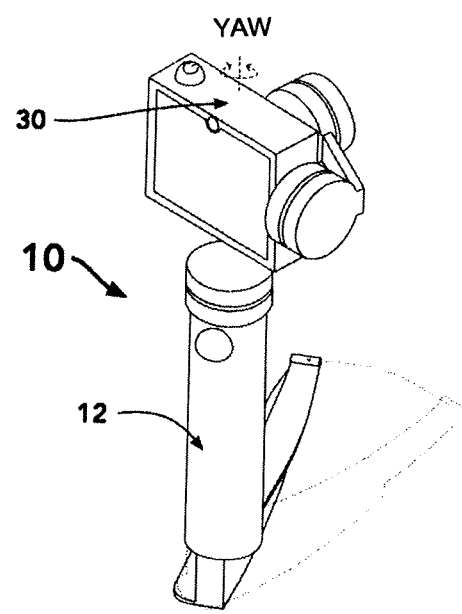
FIG. 9 is an isometric view of the laryngoscope device according to the first embodiment of FIG. 1 as the display monitor pivots about a yaw axis relative to the handle.
Figure 10:
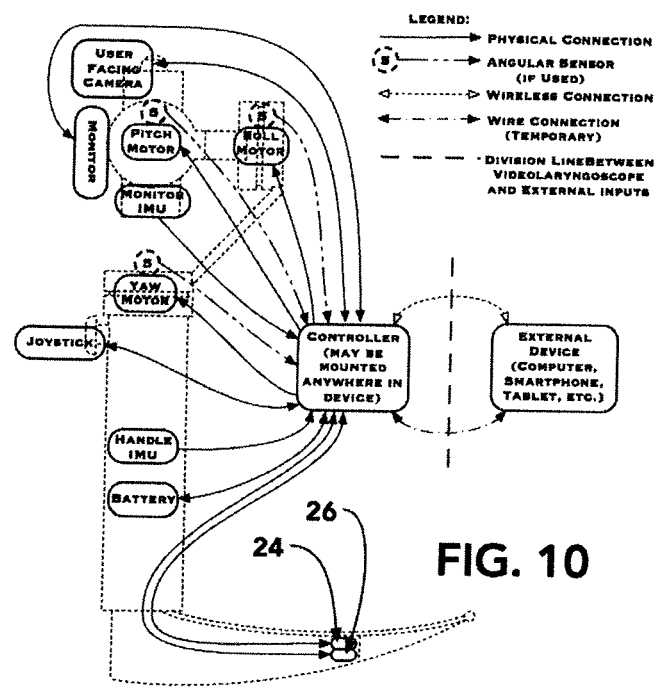
FIG. 10 is a schematic representation of the various components of the laryngoscope device according to the first embodiment of FIG. 1.
Figure 11:
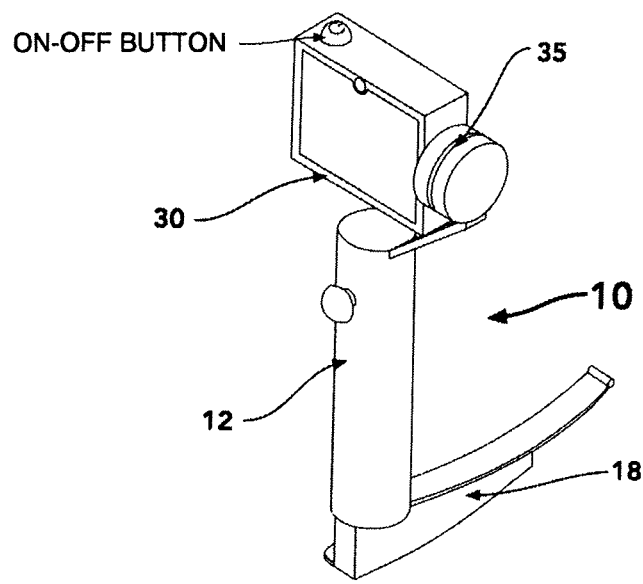
FIG. 11 is an isometric view of a second embodiment of the laryngoscope device in which the display monitor only pivots about the pitch axis.
Figure 12:
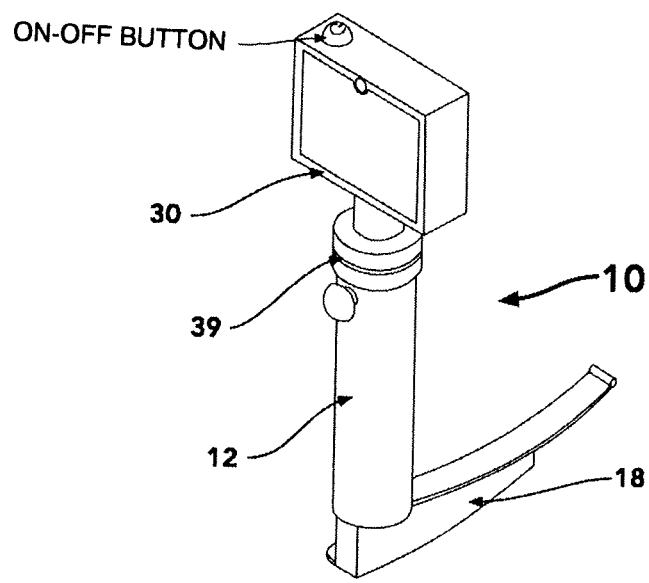
FIG. 12 is an isometric view of a further embodiment of the laryngoscope device in which the display monitor only pivots about the yaw axis.
Figure 13:
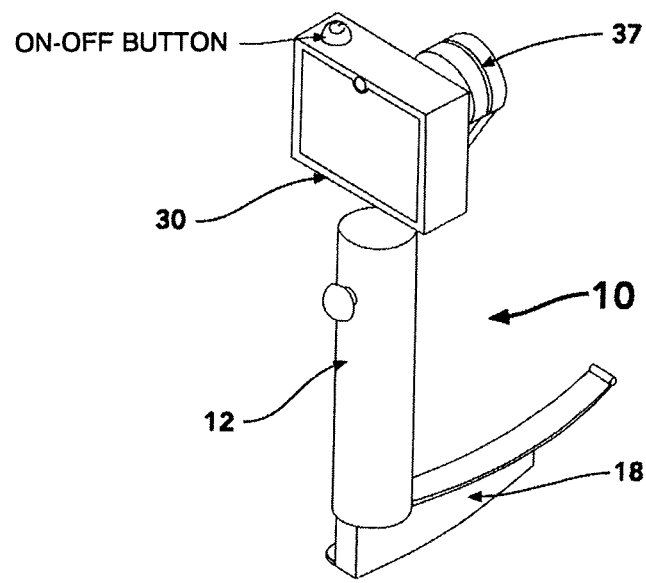
FIG. 13 is an isometric view of a further embodiment of the laryngoscope device in which the display monitor only pivots about the roll axis.
Figure 14:
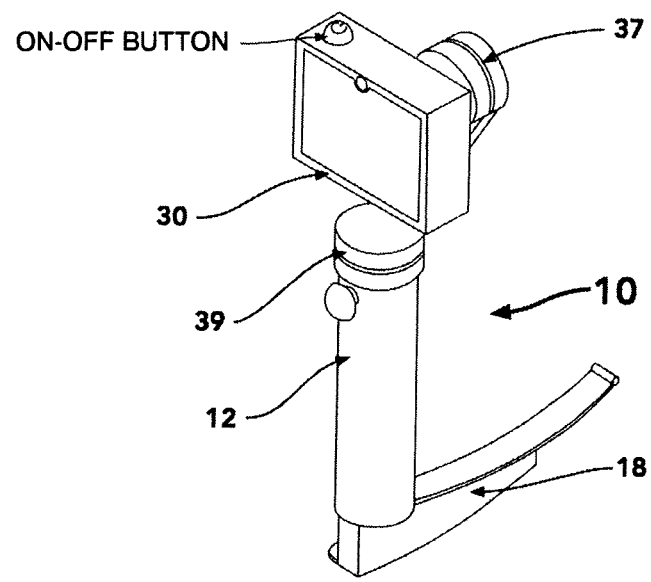
FIG. 14 is an isometric view of a further embodiment of the laryngoscope device in which the display monitor only pivots about the roll axis and the yaw axis.
Figure 15:
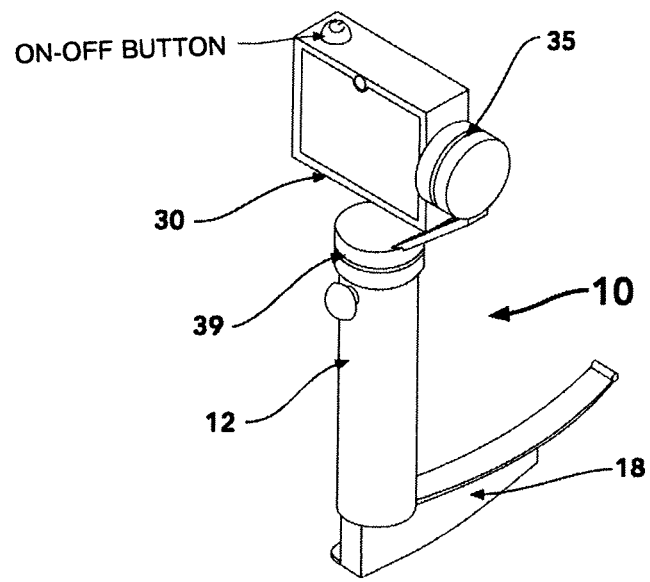
FIG. 15 is an isometric view of a further embodiment of the laryngoscope device in which the display monitor only pivots about the pitch axis and the yaw axis.

The initial target orientation stored on the controller may be a neutral position in which the display monitor is centred about all three adjustment axes relative to the handle. The neutral position is shown in FIG. 3 in which the display surface of the monitor is parallel to the longitudinal axis of the handle and perpendicular to the longitudinal direction of the blade protruding from the handle. When the handle is vertically oriented, the pitch axis and the roll axis are thus oriented in a horizontal orientation perpendicularly to one another and to the yaw axis.

Typically, the operator will calibrate the target orientation at the start of each use such that the target orientation corresponds to a preferred orientation of the display monitor relative to the surroundings locating the operator therein. This may be accomplished by an initial calibration routine executed by the programming on the controller in which the display monitor starts in the neutral position of FIG. 3 but can be deflected away from the neutral position using various means of operator input. Once the display monitor has been repositioned by the operator in a desirable orientation, the current orientation of the display monitor is stored as the target orientation.

Once calibrated, the controller receives data from all of the components of the sensor device to detect any movement of the display monitor away from the target orientation. In response to any detected angular movement away from the target orientation about any one of the three axes, the controller will generate a suitable control signal to the motors associated with the one or more axes about which angular movement is detected to compensate for the detected movement and return the display monitor back to the target orientation.

The initial target orientation stored on the controller can be calibrated by various means of operator input. In one example, a joystick 64 is supported on the handle so as to be adapted for being readily engaged and controlled by the thumb on the hand of a user which is gripped about the handle during normal operation of the laryngoscope device. The joystick may operate in combination with another button which controls which axis the joystick 64 is associated with. When the joystick is associated with one of the prescribed axes of the pivot assembly, lateral displacement of the joystick in two opposing directions corresponds to an operator input which adjusts the target orientation in two opposing direction about the corresponding axis with which the joystick is associated.

In a further embodiment, the controller may be equipped with a wireless transceiver to allow wireless communication with an external mobile computer device, for example a smartphone, a tablet or other computer having suitable operator input controls thereon. In this instance, the operator can select a preferred target orientation using the controls of the mobile computer device and this selected target orientation is then communicated to the controller once a wireless communication is established between the controller of the device 10 and the mobile computer device.

In a further instance, the controller may include a calibration mode in which the operator can simply manually reposition the display monitor into a desired orientation relative to the handle. Once the operator confirms that the display monitor is in a preferred orientation through an operator input on the controller, the controller will store the current position of the display monitor as the target orientation.

Although the gimbal assembly according to the first embodiment of FIGS. 1 through 10 is shown with three pivot assemblies supporting the display monitor for pivotal movement about three axes relative to the handle, typically the most beneficial control of the display monitor orientation is the control of the angular movement about the pitch axis relative to the handle.

Typically, all components of the controller and sensor assembly are commonly connected to the battery within the handle to provide all electrical power to the device 10 as a whole.

In yet further embodiments, a tracking camera 66 is supported on the display monitor for movement together with the display monitor relative to the handle. The tracking camera is oriented to face perpendicularly outward from the display surface of the display monitor for capturing images of an operator viewing the display. Suitable programming is stored on the controller for being executed by the controller for identifying the face of an operator in the images captured by the tracking camera and for generating control signals to the motors for centering of the identified operator in the images relative to the frame of the image. In this manner the monitor orientation is automatically adjusted by the controller to maintain the target orientation which results in the display surface facing the operator. Similarly to the previous embodiment the target orientation corresponds to a selected orientation of the monitor relative to a reference target, such as the surrounding environment in the previous embodiment or the operator in the tracking camera embodiment.

As described herein, to actively ensure that the monitor will remain in the same position relative to the horizon and will not be affected by the rotational position of the handle, the system must actively sense the position of the handle and the monitor, interpret this information and use this information to actively keep the monitor in a stable position relative to the handle. This is accomplished by a Micro-Electro-Mechanical System (MEMS) which takes a mechanical force and translates it into an electrical signal which then can be fed into a computer. The type of MEMS used in this design are typically called an Inertial Measurement Unit (IMU) which uses a 3-axis accelerometer and a 3-axis gyroscope to sense the position and mechanical forces applied to the handle and monitor. This information is fed into a computer (called a controller) which the interprets this information to keep the monitor in a fixed position relative to the horizon. In it's simplest iteration, the system can keep the monitor level to the horizon regardless of the position of the handle. During the dynamic process of intubation, the handle will move through a variety of positions and orientation as the tip of the VL blade is placed through the mouth, over the tongue, past the oropharynx and finally into position to provide a view of the larynx. At the same time, the position of the patient and user remains fixed. This system will use an IMU to sense the position of the monitor and, possibly, a second IMU to sense the position of the handle. In addition to the IMUs, this system may or may not use angle sensors mounted to each of the three gimbal axes as input sensor information. These IMUs/angle sensors will feed information into the controller which will use firmware to interpret the IMU/angle sensor data and send out signals to motors which are mounted on each of three gimbal pivot axes which are mounted orthogonal to each other. In this device, the outermost gimbal is mounted to the handle, the innermost gimbal is mounted to the monitor. The IMUs/angle sensors will send positional data from the monitor and the handle to the controller multiple times per second and the controller will in turn send out commands to the three motors multiple times per second to keep the orientation of the monitor level relative to the horizon. In its ideal iteration, the system can keep the position of the monitor fixed relative to the horizon in any position, not just level. This is important as users are of varying heights and use different patient positions and so functionality to allow the user to customize the position of the monitor relative to the horizon is essential. This requires input to the controller to allow the user to affect the position of the monitor relative to the horizon. This could be completed prior to the intubation attempt by using a physical connection (i.e. cable) between the controller and an external device (i.e. computer, tablet, smartphone, etc.). This would allow the user to customize not only the position of the monitor relative to the horizon but also the way the motors respond (speed, angular acceleration, etc.). This could also be completed prior to the intubation attempt by using a wireless connection between the controller (via a wireless module—Wi-Fi, Bluetooth, etc.) and an external device (i.e. computer, tablet, smartphone, etc.). This would allow the user to customize not only the position of the monitor relative to the horizon but also the way the motors respond (speed, angular acceleration, etc.). The user could adjust the position of the monitor relative to the horizon using an input device (joystick, etc.) physically mounted on the device itself. Finally, through the user facing camera and face recognition software on the controller firmware, the controller could keep the monitor facing the user always, regardless of the position of handle (see FIG. 10).

Figure 16:
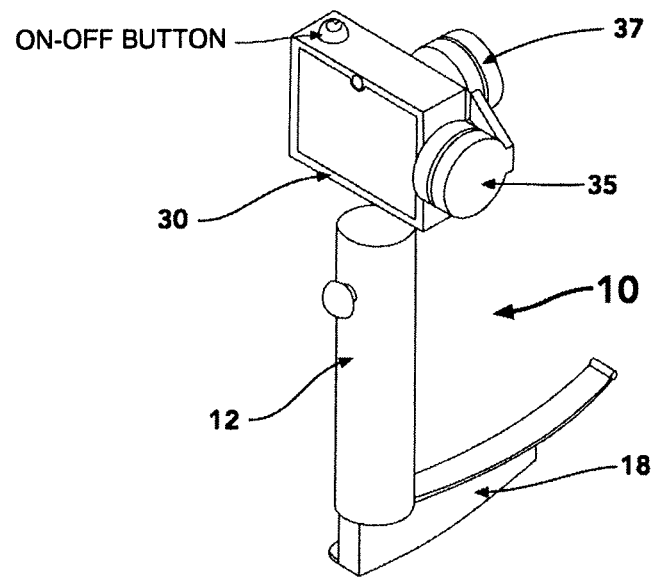
FIG. 16 is an isometric view of a further embodiment of the laryngoscope device in which the display monitor only pivots about the pitch axis and the roll axis.

Turning now to FIGS. 11 through 16, the design also allows for an option to only control the position of the monitor in one or two axes, not just three. In typical intubation attempts the handle's position is rotationally varied in only one plane and so pitch adjustment of the monitor module would be potentially the only axis required. In this case, a one axis gimbal with a pitch gimbal motor is only required (see FIG. 11). But one could also have a yaw only gimbal (see FIG. 12), a roll only gimbal (see FIG. 13), a yaw/roll gimbal (FIG. 14), a yaw/pitch gimbal (FIG. 15) or finally a roll/pitch gimbal (FIG. 16).

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A laryngoscope device comprising:
a handle which is elongate in a longitudinal direction between opposing first and second ends so as to be arranged to be gripped in a hand of an operator;
a laryngoscope blade supported on the first end of the handle so as to extend outwardly from the handle transversely to the longitudinal direction of the handle;
a camera supported on laryngoscope blade so as to be arranged to capture video images;
a display monitor for displaying the video images captured by the camera;
at least one pivot assembly comprising:
a pivot coupling the display monitor to the second end of the handle for pivotal movement about a respective axis of the pivot; and
a motor for controlling angular position of the display monitor relative to the handle about the axis of the pivot;
a controller having the target orientation stored thereon, the target orientation defining a selected orientation of the display monitor relative to a reference target;
a sensor device arranged to detect movement of the display monitor away from a target orientation relative to the reference target; and
the controller being adapted to operate the motor of said at least one pivot assembly to return the display monitor to the target orientation relative to the reference target responsive to detection by the sensor device that the display monitor has been displaced away from the target orientation resulting from a movement of the handle relative to the reference target away from a previous position of the handle relative to the reference target.

2. The laryngoscope device according to claim 1 wherein the target orientation stored on the controller is controllably adjustable by the operator.

3. The laryngoscope device according to claim 2 wherein the target orientation is adjustable through an operator input supported externally on the laryngoscope device.

4. The laryngoscope device according to claim 3 wherein the operator input is supported on the handle.

5. The laryngoscope device according to claim 3 wherein the operator input comprises a joystick.

6. The laryngoscope device according to claim 3 wherein the operator input is located so as to be adapted to be readily accessible by a thumb of a hand of the operator gripping the handle of the laryngoscope device therein.

7. The laryngoscope device according to claim 2 wherein the target orientation stored on the controller is adjustable through a wireless connection with an external mobile computer device.

8. The laryngoscope device according to claim 1 wherein the sensor device includes an inertial measurement unit supported in fixed relation to the display monitor so as to be arranged to measure accelerations acting on the display monitor and wherein the controller uses the measured accelerations acting on the display monitor in controlling operation of the motor of said at least one pivot assembly.

9. The laryngoscope device according to claim 8 wherein the sensor device further comprises a second inertial measurement unit supported in fixed relation to the handle so as to be arranged to measure accelerations acting on the handle and wherein the controller uses the measured accelerations acting on the handle in controlling operation of the motor of said at least one pivot assembly.

10. The laryngoscope device according to claim 9 wherein the sensor device further comprises an angular position sensor supported on the pivot of said at least one pivot assembly to measure angular position of the display monitor relative to the handle about the axis of the pivot of said at least one pivot assembly, and wherein the controller uses the measured angular position in controlling operation of the motor of said at least one pivot assembly.

11. The laryngoscope device according to claim 10 wherein said at least one pivot assembly includes one pivot in which the pivot axis thereof is a pitch axis oriented parallel to a display surface of the display monitor and transversely to the handle.

12. The laryngoscope device according to claim 11 wherein said at least one pivot assembly includes one pivot in which the pivot axis thereof is a roll axis oriented perpendicularly to a display surface of the display monitor and transversely to the handle.

13. The laryngoscope device according to claim 1 wherein said at least one pivot assembly includes one pivot in which the pivot axis thereof is a yaw axis oriented parallel to the longitudinal direction of the handle.

14. The laryngoscope device according to claim 1 wherein said at least one pivot assembly includes two pivots in which the pivot axes thereof are oriented perpendicularly to one another.

15. The laryngoscope device according to claim 1 wherein said at least one pivot assembly includes three pivots in which the pivot axes thereof are oriented transversely to one another.

16. The laryngoscope device according to claim 1 further comprising a tracking camera supported on the display monitor so as to be arranged to capture an image of the operator in which the operator defines the reference target and tracking programming stored on the controller so as to be executable by the controller to identify the operator in the images captured by the tracking camera and to operate the motor of said at least one pivot assembly so as to maintain the operator centered within the images captured by the tracking camera.

17. The laryngoscope device according to claim 1 further comprising a battery supported on the handle which is operatively connected to supply electrical power to each one of the camera, the display monitor, the sensor device, the controller, and the motor of said at least one pivot assembly.

18. The laryngoscope device according to claim 1 wherein the reference target comprises a surrounding environment.

* * * * *